(12) United States Patent
Komurasaki (10) Patent No.: US 7,435,590 B2
(45) Date of Patent: Oct. 14, 2008

(54) MONOCLONAL ANTIBODY AND HYBRIDOMA PRODUCING THE SAME

(75) Inventor: Toshi Komurasaki, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 93 days.

(21) Appl. No.: 10/548,591

(22) PCT Filed: Mar. 15, 2004

(86) PCT No.: PCT/JP2004/003424

§ 371 (c)(1),
(2), (4) Date: Sep. 12, 2005

(87) PCT Pub. No.: WO2004/081047

PCT Pub. Date: Sep. 23, 2004

(65) Prior Publication Data

US 2006/0252105 A1    Nov. 9, 2006

(30) Foreign Application Priority Data

Mar. 14, 2003 (JP) ............................. 2003-070864

(51) Int. Cl.
C12N 5/06 (2006.01)
C12N 5/16 (2006.01)
A61K 39/395 (2006.01)
A61K 39/00 (2006.01)

(52) U.S. Cl. .................. 435/330; 424/138.1; 424/141.1

(58) Field of Classification Search ....................... None
See application file for complete search history.

(56) References Cited

U.S. PATENT DOCUMENTS 5,783,417 A    7/1998    Komurasaki et al.

2002/0040127 A1 *    4/2002    Jiang et al. ................. 530/350

FOREIGN PATENT DOCUMENTS

| JP | 2001-149079 A | 6/2001 |
|----|----|----|
| WO | WO 01/62918 A2 | 8/2001 |
| WO | WO 01/96390 A2 | 12/2001 |
| WO | WO 03/057160 A2 | 7/2003 |

OTHER PUBLICATIONS

H. Toyoda et al., "Distribution of mRNA for human epiregulin a differentially expressed member of the epidermal growth factor family", *Biochemical Journal*, vol. 326, part 1, Aug. 15, 1997, pp. 69 to 75.

Komurasaki T, "Epiregulin binds to epidermal growth factor receptor and ErbB-4 and induces tyrosine phosphorylation of epidermal growth factor receptor, ErbB-2, ErbB-3 and ErbB-4", Oncogene, 15, (23): Dec. 4, 1997, pp. 2841-2848.

Yuji Shirakata, et al., "Epiregulin, a Novel Member of the Epidermal Growth Factor Family, Is an Autocrine Growth Factor in Normal Human Keratinocytes", The Journal of Biological Chemistry, 2000, 275(8):5748-5733.

Toshi Komurasaki, et al., "Mechanism of Growth Promoting Activity of Epiregulin in Primary Cultures of Rat Hepatocytes", Growth Factors, 2002, 20(2):61-69.

* cited by examiner

*Primary Examiner*—David J. Blanchard
*Assistant Examiner*—Anne M. Gussow
(74) *Attorney, Agent, or Firm*—Sughrue Mion, PLLC (57) ABSTRACT

The present invention establishes a simple and a highly sensitive detection method for hEPR and provides a novel detection method for human tumors which express hEPR. In particular, the present invention provides a monoclonal antibody which specifically recognizes human epiregulin (hEPR), hybridoma which produces the monoclonal antibody, and a highly sensitive detection method for hEPR using the monoclonal antibody.

3 Claims, 7 Drawing Sheets

MONOCLONAL ANTIBODY AND HYBRIDOMA PRODUCING THE SAME

TECHNICAL FIELD

The present invention relates to a monoclonal antibody (MoAb) which specifically recognizes human epiregulin (hEPR), a hybridoma which produces the MoAb and an immunological measurement method to specifically detect hEPR in samples using a hEPR-polyclonal antibody (hEPR-PoAb) which recognizes hEPR and the MoAb.

BACKGROUND ART

It has been known that there are certain gene abnormalities which occur with specificity and high frequency in cancer cells, and if a protein (proteins) which is caused by the gene abnormality is found, then such a protein may be a target molecule for cancer diagnosis and therapy. Among them, a group of molecules which belong to epidermal growth factor (EGF) family and their receptor ErbB family molecules have been the target molecules for cancer diagnosis and therapy as they are involved in the growth of cancer cells and related to malignancy. (J. Clin. Oncol., 17, 2639-2648 (1999); Biochem. Biophys. Acta., 1198, 165-184 (1994); Science, 244, 707-712 (1989); Anticancer Res., 20:91-95 (2000); Front. Biosci., 1;6:D685-707 (2001)).

It has been reported that epiregulin (EPR), a member of EGF family, has a bi-functional character that it promotes the growth of normal cells and inhibits the growth of certain cancer cells in vitro, and that the expression level of EPR (mRNA) in normal cells is extremely low except in the placenta and monocytes, but high in certain cancer cells (see, for example, The Journal of Biological Chemistry, 1995, Vol. 270, p. 7495-7500; The Biochemical Journal, 1997, Vol. 326, p. 69-75).

Further, in the clinical field, it is indicated that epiregulin may be a useful marker for cancer diagnosis because its expression is high in cancer of bladder cancer and the pancreatic cancer, (see, for example, Biochemical and Biophysical Research Communications, 2000, Vol. 14, 273 (3), p. 1019-1024; AntiCancer Research, 2000, January-February, 20 1A9: p. 91-95; Cancer Research, 2001, Vol. 61, p. 6227-6233).

Up until now, there have been reports that EPR polypeptide is detected using polyclonal antibodies (hEPR-PoAb) which recognize human epiregulin (hEPR) (see, for example, The Journal of Biological Chemistry, 1995, Vol. 270, p. 7495-7500; The Biochemical Journal, 1997, Vol. 326, p. 69-75), but they are not the methods with high sensitivity and high throughput because they require concentration operations, labeling with radioisotopes and the like, and there is no report of detecting EPR polypeptide in the living body. Thus, the establishment of a simple and highly sensitive method of detecting hEPR may offer useful means, as a cancer diagnosis method, for early detection of cancer.

DISCLOSURE OF THE INVENTION

The amino acid sequence homology between EPR and other EGF family member proteins is known to be 24 to 50% (see The Journal of Biological Chemistry, 1995, Vol. 270, p. 7495-7500). Furthermore, the sequence homology of EPR between the species is very high, for example, EPRs of human and mouse are different in only 6 out of 46 amino acid residues. The detection method for EPR by using the polyclonal antibodies described above requires complicated procedures, and cannot differentiate human and mouse EPR. Also, the sensitivity of the conventional detection methods is at most 1 ng/ml, and it is therefore impossible to detect EPR in the living body.

The objective of the present invention is to establish a simple and highly sensitive detection method for hEPR and to utilize the method of detecting human tumors. In particular, the present invention provides a simple method of detecting hEPR at a picogram level that is useful for detecting tumors, and the like.

The present inventors have earnestly studied to solve the problems described above and finally obtained two hybridomas (1C3, 3E8) producing monoclonal antibodies (MoAb) which specifically recognize hEPR. Further, sandwich enzyme-linked immunosorbent assay method (S-ELISA) is established by combining the MoAb and hEPR-PolyAb, and a detection system, which is highly sensitive and high throughput, is completed.

Thus, the present invention provides following (1) to (9).

(1) A hybridoma producing a monoclonal antibody which specifically recognizes human epiregulin (hEPR).

(2) The hybridoma according to (1), which has an accession number of FERM BP-08647.

(3) The hybridoma according to (1), which has an accession number of FERM BP-08648.

(4) A monoclonal antibody produced by the hybridoma according to any one of (1) to (3).

(5) A monoclonal antibody, which recognizes an epitope that is recognized by the monoclonal antibody produced by the hybridoma according to (2) or (3), and specifically recognizes hEPR.

(6) A method of specifically detecting hEPR in a sample in vitro, characterized in that the monoclonal antibody according to (4) and a polyclonal antibody that recognizes hEPR (hEPR-PoAb) are used.

(7) A method of detecting hEPR-expressing cells in vitro, characterized in that the monoclonal antibody according to (4) is used.

(8) The method according to (7), wherein the hEPR-expressing cells are a human tumor.

(9) A kit for detecting a human tumor comprising the monoclonal antibody according to (4).

The contents of the specification and/or drawings of the Japanese Patent Application No. 2003-070864, which is a basis of the priority of the present application, are hereby incorporated by reference in its entirety.

BEST MODE FOR CARRYING OUT THE INVENTION

While the present invention is described in detail below, those skilled in the art can practice the present invention in various embodiments using known techniques in the art and the present invention is not limited to the following embodiments.

The term "hEPR" as used herein means a precursor, mature form or fragment of human epiregulin, unless otherwise stated. The "precursor" means a membrane bound form before cleavage by an enzyme, and the "mature form" means the polypeptide with 46 amino acid residues (SEQ ID NO:1) released from the cell membrane. The fragment contains 20 amino acid residues or more, or preferably with 30 amino acid residues or more of the polypeptide and must contain a sequence specific to human epiregulin. The sequence specific to human epiregulin does not mean to be limited, but includes, for example, a sequence containing the 2nd, 11th, 26 to 29th and 39th amino acids of the amino acid sequence of SEQ ID NO:1, which are known to be different when human epiregulin and mouse epiregulin are compared. The fact that the amino acids at these sites are different between human and mouse is described in Patent Application WO94/29340 of the same applicant. The fragments having the amino acid sequence containing these sites take different higher structures when the EPR fragments derived from human and mouse are compared. "Human epiregulin" and "mouse epiregulin" are the polypeptides with the same amino acid sequence as EPR naturally present in human and mouse, respectively. However, they are not necessarily limited to proteins extracted from the natural sources, but it is intended that they include, for example, recombinants and synthetic polypeptides.

The term "specifically recognize" as used herein means that hEPR is recognized (or bound), but other proteins of EGF family or non-human EPR such as mouse EPR and the like are substantially not recognized (bound). It means, for example, the precursor, mature protein, and fragmented polypeptides of hEPR are recognized (bound), but EGF and TGF-α, mouse EPR and the like are substantially not recognized (not bound). In particular, it means that its affinity for binding, compared to that against the other proteins of EGF family and non-human EPR such as mouse EPR, is 100 times or higher, preferably 1000 times or higher, more preferably 10,000 times or higher.

The term "substantially not recognized (bound)" as used herein means that the binding is not confirmed by the detection means generally used in the art or of the present invention. In particular, it means that the precursor, mature protein and fragmented polypeptide of hEPR exhibit a positive reaction to the sandwich ELISA (S-ELISA) method, the Western blot method or the like, but EGF and TGF-α of the EGF family and EPR derived from mammals other than human, such as mouse, do not show the reaction (not detected).

The term "antibody" as used herein means a polyclonal antibody (PoAb) or a monoclonal antibody (MoAb) which specifically binds to a complete full length molecule of hEPR or a hEPR fragment, or a partial fragment of these antibodies (for example, fragments (Fab or F(ab')2 or Fab') obtained by digestion with papain or pepsin, or the like) and may be produced by the method of production described below.

Hybridomas and monoclonal antibodies of the present invention may be produced as follows. Further, those skilled in the art may use suitably altered methods based on the following description and known techniques in the art.

(1) Preparation of Antigen

The amino acid sequence of hEPR antigen and the nucleotide sequence which codes for the same are described in WO94/29340. The amino acid sequence and the nucleotide sequence are shown in SEQ ID NO:1 and SEQ ID NO:2, respectively. Further, EPR is described as a tumor cell growth inhibitory factor in WO94/29340.

Recombinant human EPR may be obtained, as described in WO94/29340, by constructing an expression vector which contains a fragment of DNA (SEQ ID NO:2) coding for hEPR and by introducing and expressing the vector in a host cells, for example, not limited but preferably, *Bacillus brevis*. After the expression using *Bacillus brevis*, the culture medium is concentrated by 20 folds using an ultra-filtration membrane (1000 kDa), the pH is adjusted to 7.4 with 1 M Tris-HCl (pH 8.0) and the purification is carried out using an anion exchange column, for example, a Q-sepharose column. In this case, the pass-through fraction is adjusted to pH 5.0 and further purified by a cation exchange column, for example, an S-sepharose column. Next, purification by a reverse phase column chromatography (C4 column) is carried out so as to obtain a single band in the electrophoresis.

hEPR may also be synthesized chemically by the solid phase method (Merrifield, J. Am. Chem. Soc., Vol. 85, p 2185 (1963)) based on the amino acid sequence shown in SEQ ID NO:1. Chemical synthesis by the solid phase method is usually carried out by the standard method using an automatic peptide synthesizer.

(2) Preparation of Polyclonal Antibodies

A warm-blooded animal is immunized total 4 to 6 times with the antigen peptide solution alone or together with carriers and diluents. Examples of the warm-blooded animals used include, for example, rabbits, dogs, guinea pigs, mice, rats and the like. It is preferable to measure the antibody titer by collecting blood specimens after the third subcutaneous immunization. The measurement of antibody titer in the serum is carried out by immobilizing the peptide used as an antigen onto a 96 well microtiter plate and performing the ELISA method. After confirming that the antibody titer is raised high enough, total blood is collected, and the antibody is separated and purified by the standard method. The purification methods include, for example, ammonium sulfate precipitation, ion exchange chromatography using an anion exchanger such as DEAE cellulose and the like, gel-filtration, affinity chromatography with an active absorbent such as protein A/G and the like, and other purification methods. Further, the specificity to hEPR may be increased by purifying using a column in which hEPR is immobilized on the solid phase.

(3) Preparation of Monoclonal Antibodies

Monoclonal-antibody-producing cells are prepared by selecting from immunized warm-blooded animals an individual animal, in which the antibody titer is raised, collecting the spleen or the lymph node 2 to 5 days after the last immunization, fusing the antibody-producing cells present in these organs with myeloma cells and selecting MoAb producing hybridomas. The fusion is carried out according to the known method such as the method of Kohler et al. (Nature, 256, 495 (1975)). The myeloma cells include but not limited, for example, PAI, P3U1 (Health Science Research Resources Bank; HSRRB), Japan, Catalogue No. JCRB0113 and JCRB0708) and the like. The fusion promotion agents include polyethylene glycol (PEG) and Sendai virus (HVJ), but preferably PEG with a molecular weight 1000 to 6000. An efficient cell fusion may be achieved by adding the promotion agent at a concentration of about 10 to 80% and incubating at 20 to 40° C.

Selection of monoclonal antibody may be carried out in accordance with the known method. Generally, it is carried out in a cell culture medium for animal cells added with HAT (hypoxanthine, aminopterin, thymidine). The media for selection and growth may include, for example, PRMI1640 medium containing 10 to 20% bovine fetal serum and the like. Cells are generally cultured under 5% $CO_2$ gas at a temperature 20 to 40° C. for 5 days to 3 weeks.

The culture supernatants are collected from wells in which hybridoma cells are cultured, and antibodies reacting with the antigen peptide may be selected by the ELISA method. First, the antigen peptide is immobilized onto 96-well plates and then blocked with calf serum. After reacting the supernatant of hybridomas with Mouse Immunoglobulins/HRP (Amersham-Pharmacia) at 37° C. for 1 hour, color is developed using Tetra Methyl Benzidine Microwell Peroxidase Substrate (TMB; Funakoshi) as a substrate. After terminating the reaction by acid, absorbance at 450/540 nm is measured. The antibodies with the absorbance of about 3 are selected, and cloning is carried out by the limited dilution method.

The target hybridoma cells thus obtained are cultured and the monoclonal antibody may be obtained from the culture medium. Alternatively, the hybridoma cells may be inoculated intraperitonealy into, for example, mouse (Balb/c) and the monoclonal antibody may be obtained from the ascites.

Purification of the monoclonal antibody may be carried out in a similar manner as the conventional separation and purification of PoAb described above.

Further, the present inventors deposited two kinds of hybridomas on Sep. 25, 2002 to the International Patent Organism Depositary, National Institute of Advanced Industrial Science and Technology (AIST) (Chuoh No. 6, 1-1-1 Higashi, Tsukuba City, Ibaragi-Ken), with accession Nos. FERM P-19033 and FERM P-19034. Still further, they are moved on Feb. 27, 2004 to international depositary based on Budapest Treaty on the International Recognition of the Deposit of Microorganisms for the Purposes of Patent Procedure with accession Nos. FERM BP-08647 and FERM BP-08648.

Furthermore, monoclonal antibodies of the present invention include monoclonal antibodies which specifically recognize an epitope, which is recognized by the monoclonal antibodies produced by the hybridoma described above, especially the hybridoma with the accession Nos. BP-08647 and FERM BP-08648, and also recognize hEPR. The epitope, which is recognized by these monoclonal antibodies, contains the amino acid residues which are included in the unique sequence of hEPR described above.

The present invention provides a method of specifically detecting hEPR in a sample in vitro, characterized in that the monoclonal antibodies and the polyconal antibodies, which recognize hEPR (hEPR-PoAb) of the present invention described above, are used. The sample includes blood, body fluids, tissue extracts and the like, collected from subjects. Although not limited, the preferred method is the S-ELISA assay method, comprising a step of contacting a sample, which may contain hEPR antigen, to the monoclonal antibody of the present invention and a step of contacting the antigen-antibody complex, which is generated in the first step, to polyclonal antibodies. The steps described above may be carried out sequentially (stepwise method) or simultaneously (same time method). The S-ELISA method is described, for example, in "monoclonal antibody, hybridoma and ELISA" (Iwasaki, Tatsuo et al. Kodansha Scientific), and those skilled in the art can practice the method of the present invention based on the present description. Since the detection method of the present invention is very sensitive and able to detect hEPR at 10 pg/ml or above, the concentration of hEPR expressed in the living body (about 20 to 30 pg/ml) is high enough to be detected.

The present invention also provides a method of detecting in vitro hEPR-expressing cells, especially human tumors, characterized in that the monoclonal antibodies of the present invention described above are used. Since hEPR is secreted from the cell membrane after being expressed in the cells, hEPR may be detected in the extra cellular fluid and there is no need for the sample to contain cells.

The method described above includes a step of contacting a sample derived from human and the monoclonal antibody of the present invention and a step of detecting the presence of hEPR by determining whether or not the monoclonal antibody binds to hEPR as an indicator. The target human tumors include, for example, cancer of the lung, large intestine, bladder, uterus, colon and the like, but not limited to those.

Since the detection method of the present invention is characterized in the high sensitivity, the detection can be carried out easily and fast without needs for sample manipulations such as concentration and the like. In the present method, samples containing hEPR at the concentration of 10 pg/ml or above may be detected by the S-ELISA method and the like, but it is preferable for the sample to contain 25 pg/ml or more for sure detection.

Using the detection method of the present invention, it is possible to determine whether or not the specific tumor cells or the like express hEPR, and if they do, the level of expression. Further, it may be possible to contribute elucidating the relation between the expression of hEPR and the mechanism of tumorigenesis. Still further, based on the data of tumor cells which express hEPR at a high level and of the expression level in normal cells, the presence of a tumor in the particular subject can be detected.

The present invention also provides a kit for detecting human tumor including the monoclonal antibody of the present invention.

The kit of the present invention may appropriately include, in addition to the monoclonal antibody of the present invention described above, polyclonal antibodies, a buffer, a coloring agent, a labeling reagent, a diluent and the like. Preferably the kit in the present invention is the kit for performing S-ELISA.

As will be shown below, the present invention is explained more concretely with embodiments, but as described above, the present invention is not limited to these examples.

EXAMPLE 1

Preparation of Hybridomas

One hundred μl of the recombinant hEPR (1 mg/ml) (prepared by the method described in WO94/29340) in saline was mixed with an equal volume of Freund's complete adjuvant, emulsified and inoculated to the back of a mouse (Balb/c, 6 weeks of age). After 2 weeks, the mouse was re-immunized with a mixture of the 50 μl of the saline solution of antigen peptide (hEPR, 1 mg/ml) and Freund's incomplete adjuvant, emulsified by ultrasonic treatment, and after that, additional immunizations were carried out every week. On 40 days after immunization, the spleen was removed, the lymphocytes were harvested in PRM1640 medium (supplemented with penicillin and streptomycin) and treated with 0.17 M ammonium chloride to remove red blood cells. Isolated lymphocytes were fused with myeloma cells P3U1 strain derived from a mouse bone marrow tumor by the polyethylene glycol method (PEG4000) to obtain hybridoma cells. The hybridoma cells thus obtained were suspended in HAT medium with feeder cells and then distributed to 96-well plates and cultured for 15 days.

EXAMPLE 2

Screening for the Monoclonal Antibody

The culture medium supernatants were recovered from wells in which the hybridoma cells obtained in the Example 1 were cultured, and MoAbs which react with the antigen peptide by the ELISA method were selected.

At first, 100 µl of 10 µg/ml antigen peptide was added to each well of 96-well plates, immobilized to the solid phase after keeping at 4° C. overnight and blocked with 200 µl of 10% calf serum at 37° C. overnight. One hundred µl of the culture medium supernatant of hybridoma cells was added to each well, reacted at 37° C. for 2 hours, and then horse radish peroxidase (HRP)-conjugated anti-mouse antibody (Amersham-Pharmacia), which was diluted 1000 folds, was added and reacted at 37° C. for 1 hour. The color was developed using Tetra Methyl Benzidine Microwell Peroxidase Substrate (TMB; Funakoshi) as a substrate.

After terminating the reaction by adding 100 µl of 4N sulfuric acid, absorbance at 450 to 540 nm was measured, and the MoAbs, 1C3 and 3E8, which show the absorbance of about 3, were selected and cloned by the limited dilution method.

Mouse (Balb/c), injected with 0.5 ml pristine intraperitoneally 7 days and 3 days before, were inoculated intraperitoneally with selected MoAb-producing 1C3 or 3E8 hybridoma cells, and ascites was collected about 10 days later. The collected ascites was kept at room temperature for 30 minutes, at 4° C. overnight and centrifuged at 15,000×rpm for 10 minutes, and then the supernatant was recovered.

Figure 1:
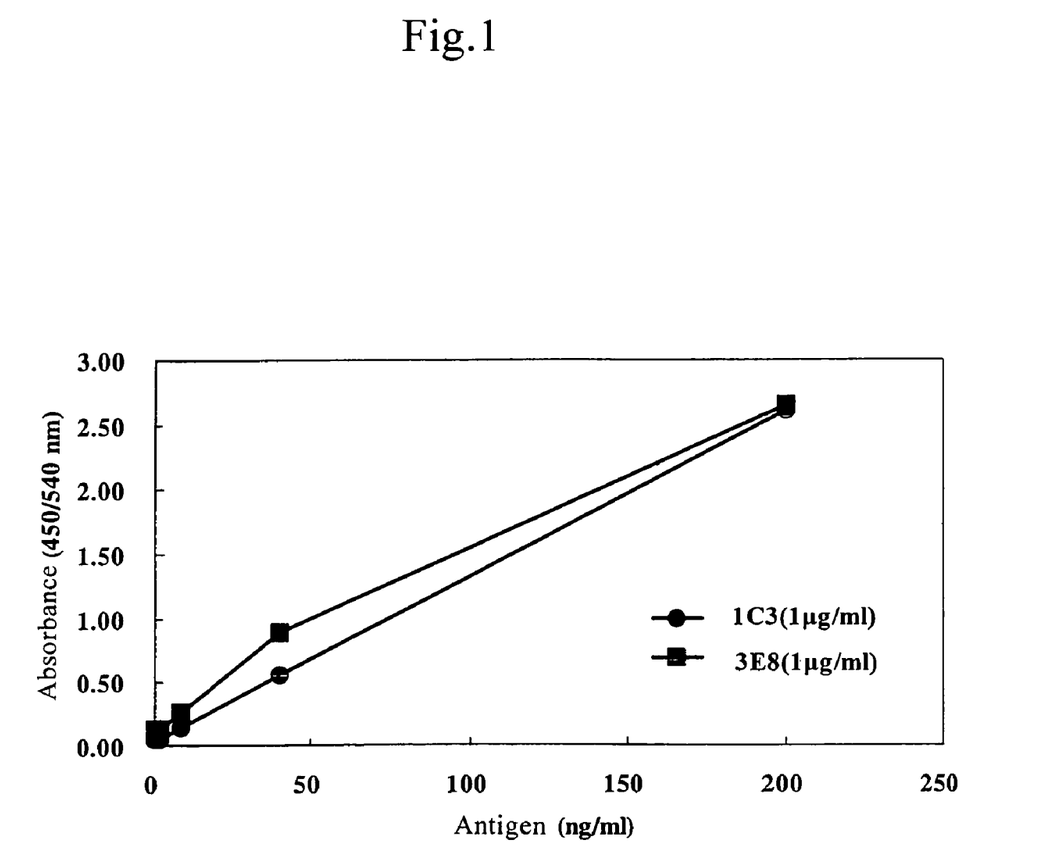
FIG. 1 shows the results of the measurement of the titer of the anti-hEPR monoclonal antibody which is produced by the hybridoma of the present invention by ELISA method.

The titers of selected 2 kinds of MoAb were measured by the ELISA method and results were shown in FIG. 1. The amount of recombinant hEPR shown on the horizontal axis was immobilized on a microwell plate, 1C3 or 3E8 (1 µg/ml) was added, and after the reaction, color was developed using horse radish peroxidase (HRP)-conjugated anti-mouse antibody and TMB. The results indicate that both of the MoAbs reacted in a concentration-dependent manner.

Further, two hybridomas which produce MoAb 1C3 and 3E8, were deposited on Sep. 25, 2002 to the International Patent Organism Depositary, National Institute of Advanced Industrial Science and Technology (AIST) (Center No. 6, 1-1-1 Higashi, Tsukuba City, Ibaragi-Ken), with the accession Nos. FERM P-19033 and FERM P-19034.

EXAMPLE 3

Preparation of Polyconal Antibodies

One ml of recombinant hEPR in saline (1 mg/ml) and 1 ml of Freund's complete adjuvant (Difco) were mixed and emulsified by ultrasonic treatment, and immunized to the back of a rabbit (Japan white, weight 2.7 kg, female; Japan Clea) in 10 separate places or more. One month later, 0.5 ml of recombinant hEPR in saline (1 mg/ml) and 0.5 ml of Freund's incomplete adjuvant (Sigma) were mixed and emulsified by ultrasonic treatment, and immunized for the second time in a similar manner as the first immunization. After the second immunization, additional immunizations were given every week with 1 ml recombinant hEPR in saline (1 mg/ml) and 1 ml of Freund's incomplete adjuvant, which were emulsified with ultrasonic treatment. Blood samples were collected one week after the immunization, kept at room temperature for 1 hour after stirring with a Pasteur pipette, kept standing at 4° C. overnight and then centrifuged at 5,000×g for 10 minutes to obtain the antiserum.

The antiserum was precipitated with 40% ammonium sulfate, dialyzed against 50 mM Tris-HCl (pH 8.0) overnight and purified by a Protein-G column (Amersham-Pharmacia) to obtain the IgG fraction. To purify the antibodies further, a column was prepared according to the conventional method based on the manufacturer's description by binding 1 mg of recombinant hEPR to about 1 ml of NHS-activated Sepharose™ 4 Fast Flow (Amersham-Pharmacia). The IgG fraction obtained as described above was adjusted to pH 8.0 and circulated through this column for 10 hours or longer, and antibodies bound to the column were eluted with 50 mM Glycine-HCl (pH 2.5)/0. 15 M NaCl. The eluted antibodies were immediately brought to neutral pH with 1 M Tris and dialyzed against 50 mM phosphate buffer (pH 7.4)/0.15 M to obtain hEPR specific antibodies.

Figure 2:
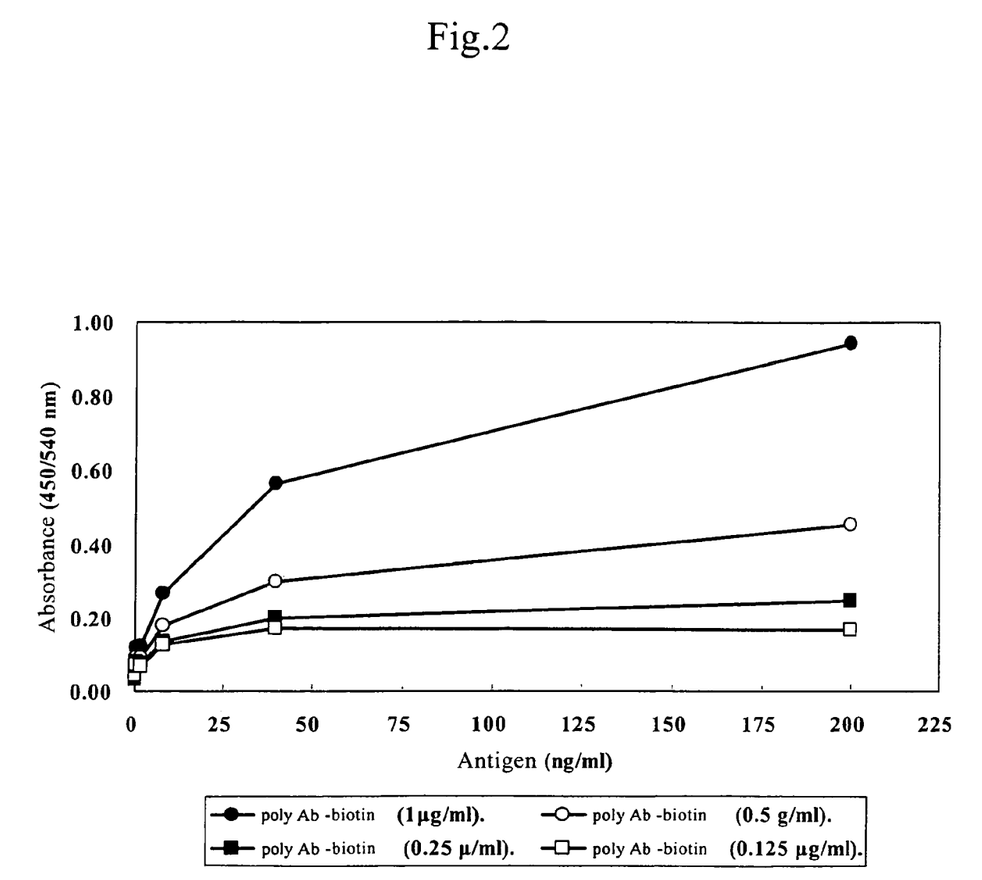
FIG. 2 shows the results of the measurement of the titer of the biotinylated-anti-hEPR polyclonal antibody.

The specific antibodies were biotinylated by a conventional method using the biotinylation reagent (Amersham-Pharmacia). The titer of biotinylated hEPR-PoAb was measured by the following method. hEPR solution of the highest concentration 200 ng/ml was diluted by 5 fold and immobilized on a 96 well microplate (100 µl/well). After blocking with 25% Block Ace (Dainippon Pharmaceutical Co.; 200 µl/well), biotinylated anti hEPR-PoAb (0.125 µg/ml to 1 µg/ml (diluted with 50% Block Ace (Dainippon Pharmaceutical Co.): 100 µl/well) was added and reacted at room temperature for 2 hours, and then Avidin-HRP (Amersham-Pharmacia) diluted 1000 fold was added at 100 µl/well and reacted at room temperature for 30 minutes. After addition of TMB, the reaction was carried out at room temperature for 30 minutes and terminated with 4N sulfuric acid. Absorbance was measured at 450 to 540 nm and the titer against the antigen immobilized on the solid phase was obtained as in Example 2. Results indicate that all of them demonstrate antigen-concentration dependent reactions, confirming that they have usable titers (FIG. 2).

EXAMPLE 4

Sandwich ELISA System

An ELISA system was constructed using the monoclonal antibody obtained in Example 2 and the polyclonal antibodies obtained in Example 3.

The monoclonal antibody, 1C3, at 1 µg/ml, was added to a microplate at 100 µl/well and incubated at 4° C. for 24 hours to immobilize to the solid phase. The wells were washed 3 times with 200 µl/well of 50 mM Tris-HCl, pH 7.5 containing 0.1% Tween 20 (TBST). Blocking was carried out by adding 25% Block Ace at 200 µl/well and incubating 4° C. for 24 hours.

In the stepwise method, the wells were washed 3 times with TBST 200 µl/well, hEPR, serially diluted by 2 fold starting from 1 ng/ml, was added and incubated at room temperature for 2 hours, then the biotinylated anti-hEPR-PoAb (1 µg/ml; 100 µl/well) was added and incubated at room temperature for 2 hours.

In the same time method, the antigen hEPR and biotinylated anti-hEPR-PoAb were added simultaneously and reacted at room temperature for 2 hours.

Figure 3:
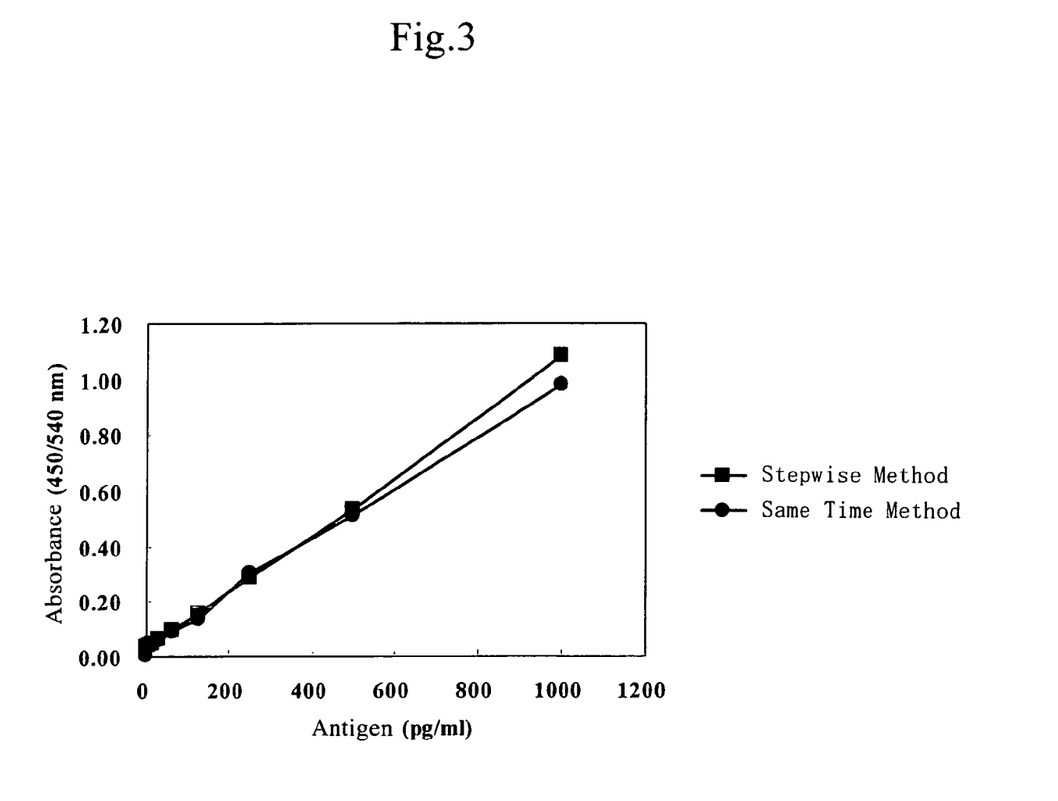
FIG. 3 shows the detection sensitivity of a sandwich ELISA (S-ELISA) system using the stepwise method and the same time method.

After washing wells 5 times with TBST, avidine-HPR (Amersham-Pharmacia) diluted 1000 fold was added at 100 µl/well and incubated at room temperature for 30 minutes. The reaction was terminated by adding 4N sulfuric acid and absorbance at 450/540 nm was measured. Results indicate that there was no difference in detection sensitivity between the stepwise method and the same time method, and both methods had sufficient sensitivity (25 pg/ml) for measuring the amount in the living body (FIG. 3). In a similar test carried out using 3E8 as the primary antibody, the results were the same.

EXAMPLE 5

Specificity of the Sandwich ELISA System

The specificity of the present system was confirmed by the method shown in Example 4 (Same time method).

Figure 4:
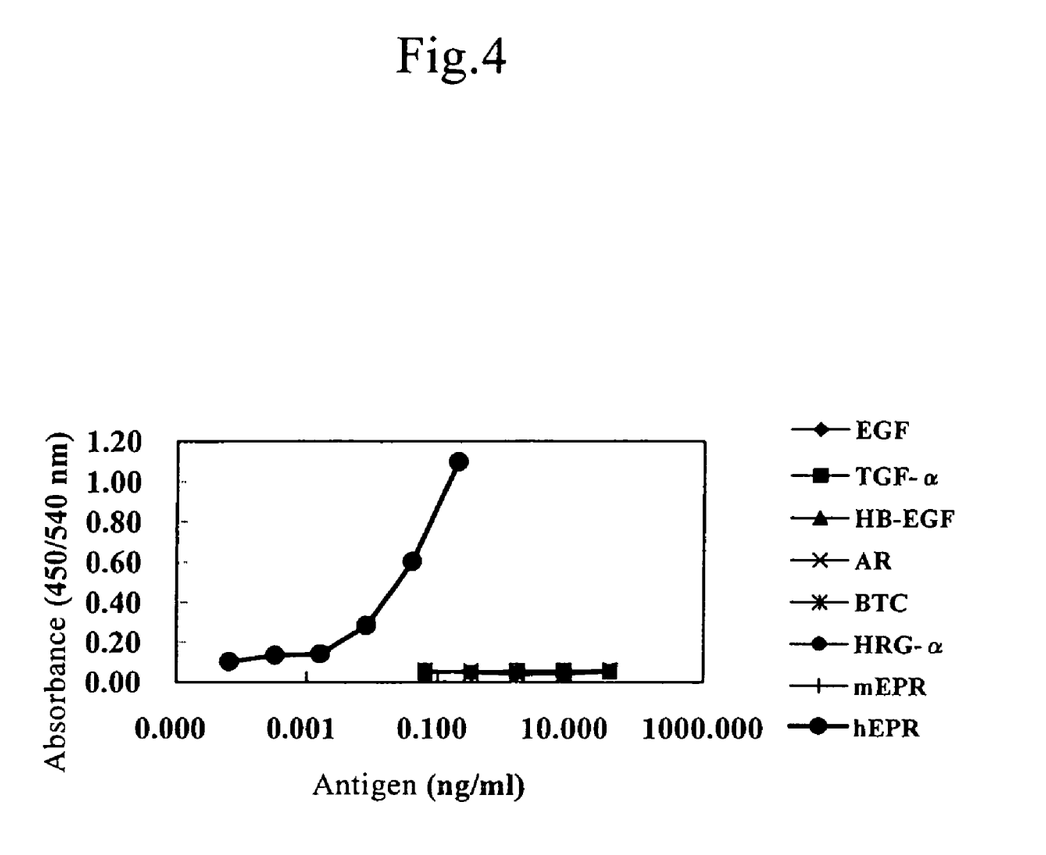
FIG. 4 shows the results of the specificity test of the present method using the 1C3 monoclonal antibody as the first antibody. In the present system, the monoclonal antibody does not react with EGF family molecules or mouse EPR, and reacts only with hEPR.

1C3 MoAb (1 µg/ml, 100 µl/well) was immobilized on wells of a microwell plate as the primary antibody, and after blocking with 25% Block Ace (200 µl/well), were added a group of molecules of EGF family member, to which EPR belongs, (6 factors; epidermal growth factor (EGF), transforming growth factor-α (TGF-α), heparin-binding EGF-like growth factor (HB-EGF), betacellulin (BTC), amphiregulin (AR), heregulin-α (HRG-α): all purchased from R&D Co. or Sigma Co.), mouse EPR (prepared in the similar way as human EPR), or human EPR, at the amount shown on the horizontal axis, together with the biotinylated hEPR-PoAb (2 µg/ml, 50 µl/well; final 1 µg/ml). The 6 members of EGF family and mouse EPR were diluted serially in 4 steps, each step by 5 fold, starting from a concentration of 200 ng/ml and added at 100 µl/well. Similarly, human EPR was diluted serially in 4 steps, each step by 5 fold, starting from a concentration of 200 pg/ml. After reacting with avidin-HPR, color was developed using TMB.

As shown in FIG. 4, hEPR was detected with high sensitivity, but other molecules that were EGF family molecules and mouse EPR were not detectable even at 1000 times higher concentrations, confirming the specificity of the present sandwich ELISA system. Similar results were obtained in the similar test using 3E8 as the primary antibody.

EXAMPLE 6

Western Blot Analysis of Human EPR in Human Serum

Figure 5:
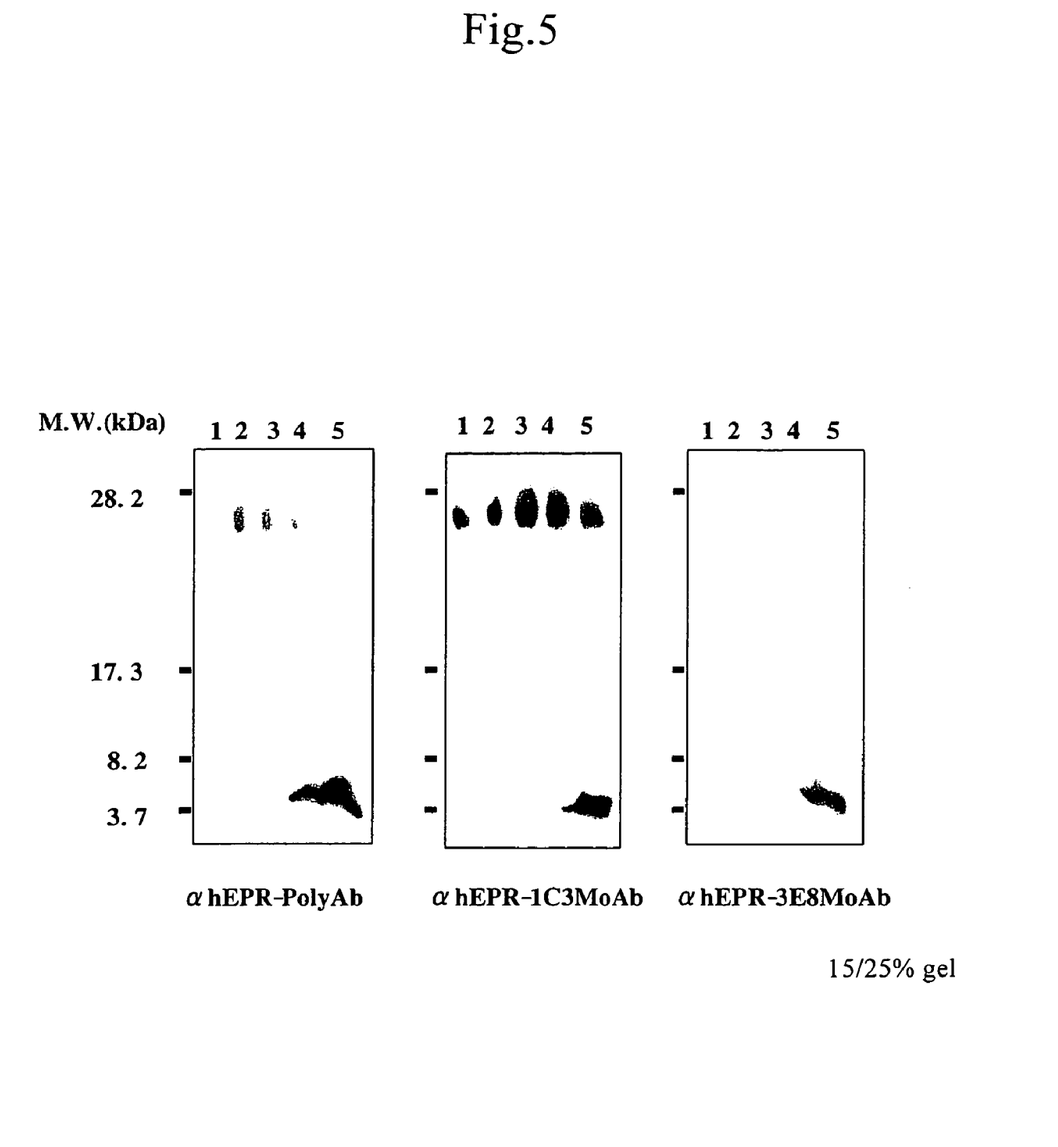
FIG. 5 shows the result of the Western blot analysis of hEPR in human serum. Positions of molecular weight markers (kDa) are shown in the left side.

Human serum (Rockland INC.) was diluted by 10 fold using 50 mM Tris-HCl buffer pH 7.4 (Gibco BRL). Recombinant hEPR was added to the diluted human serum to prepare test samples by 5 fold serial dilution so that the final concentration were in lane 1: 0 pg/ml, lane 2: 8 pg/ml, lane 3: 40 pg/ml, lane 4: 200 pg/ml, lane 5: 1000 pg/ml. The test samples thus obtained were subjected to SDS polyacrylamide gel electrophoresis (SDS-PAGE), transferred to PVDF membrane (Daiichi Pure Chemical Co.), and then analyzed by the immuno-blotting method (J. Biol. Chem., 270, 7459-7500) using antibodies, such as anti-hEPR-PoAb, MoAb1C3 and 3E8 (1 µg/ml) which recognize hERP. Results indicate that each antibody specifically detects hERP in the region of 3.7 to 8.2 kDa (FIG. 5). Although a band of about 28 kDa was detected by PoAb and 1C3 MoAb, it was regarded to be a non-specific band because the same band was detected in the lane of antigen (−).

EXAMPLE 7

Detection of Human EPR in Human Serum by the ELISA Method

Figure 6:
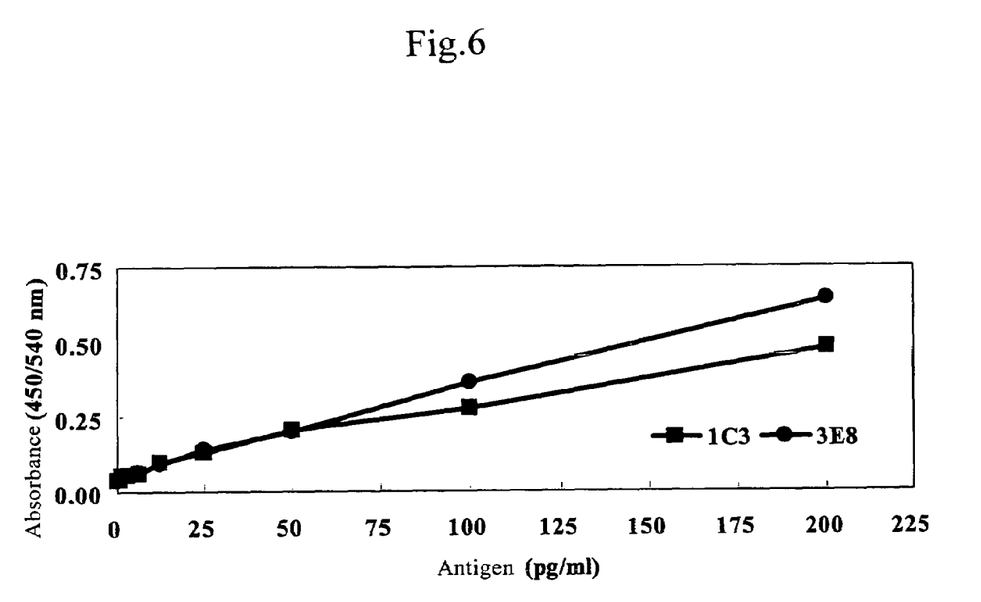
FIG. 6 shows the detection of hEPR in human serum by the S-ELISA.

The monoclonal antibody, 1C3 or 3E8, at 1 µg/ml was added to the wells of a microplate by 100 µl/well, and immobilized to solid phase by incubating 4° C. for 24 hours. The plate was washed 3 times with 200 µl/well of 50 mM Tris-HCl, pH 7.5 containing 0.1% Tween 20 (TBST) and blocked by adding 200 µl/well of Block Ace and incubating at 4° C. for 24 hours. After washing wells 3 times with 200 µl/well of TBST, hEPR in 2 fold diluted human serum was serially diluted by 2 fold starting from 400 pg/ml and added at 50 µl/well. At the same time the biotinylated anti-hEPR-PoAb (2 µg/ml) was added at 50 µl/well, and incubated at room temperature for 2 hours. After washing 5 times with TBST, 1000 fold diluted Avidin-HRP (Amersham-Pharmacia) was added at 100 µl/well, and reacted at room temperature for 30 minutes. The reaction was terminated with 4N sulfuric acid, color was developed with TMB and the absorbance was measured at 450/540 nm. Results were shown in FIG. 6 indicating that hEPR at a concentration of 25 pg/ml can be detected sufficiently by any of 1C3 and 3E8.

EXAMPLE 8

Detection of EPR Produced by Cultured Human Cancer Cells

Various culture cells derived from mouse (IC38, RAW264.7, NIH3T3 clone T7, MoAb3) and human (T-24, A-549, HCT116, colo205, colo201, HeLa, NB69, A431, SK-BR-3, MDA-MB-468, KB, TR-13), were cultured for 3 days in a culture medium containing 10% bovine calf serum starting from $10^6$ cells/10 ml/dish, and the culture media were subjected to hEPR detection by the S-ELISA method.

1C3 MoAb (1 µg/µl) was immobilized to the solid phase at 100 µl/well, and, after blocking, 50 µl of various cell culture media and 50 µl of the biotinylated hEPR-PoAb (2 µg/ml) were added to a well simultaneously and incubated at room temperature for 2 hours. Hereinafter the operations were similar to those in Example 4. As controls, the similar operations were carried out on sera with or without additional hEPR (10% FBS, human serum, 0.1% BSA (hEPR 1 ng/ml), human serum (EPR 1 ng/ml)).

Figure 7:
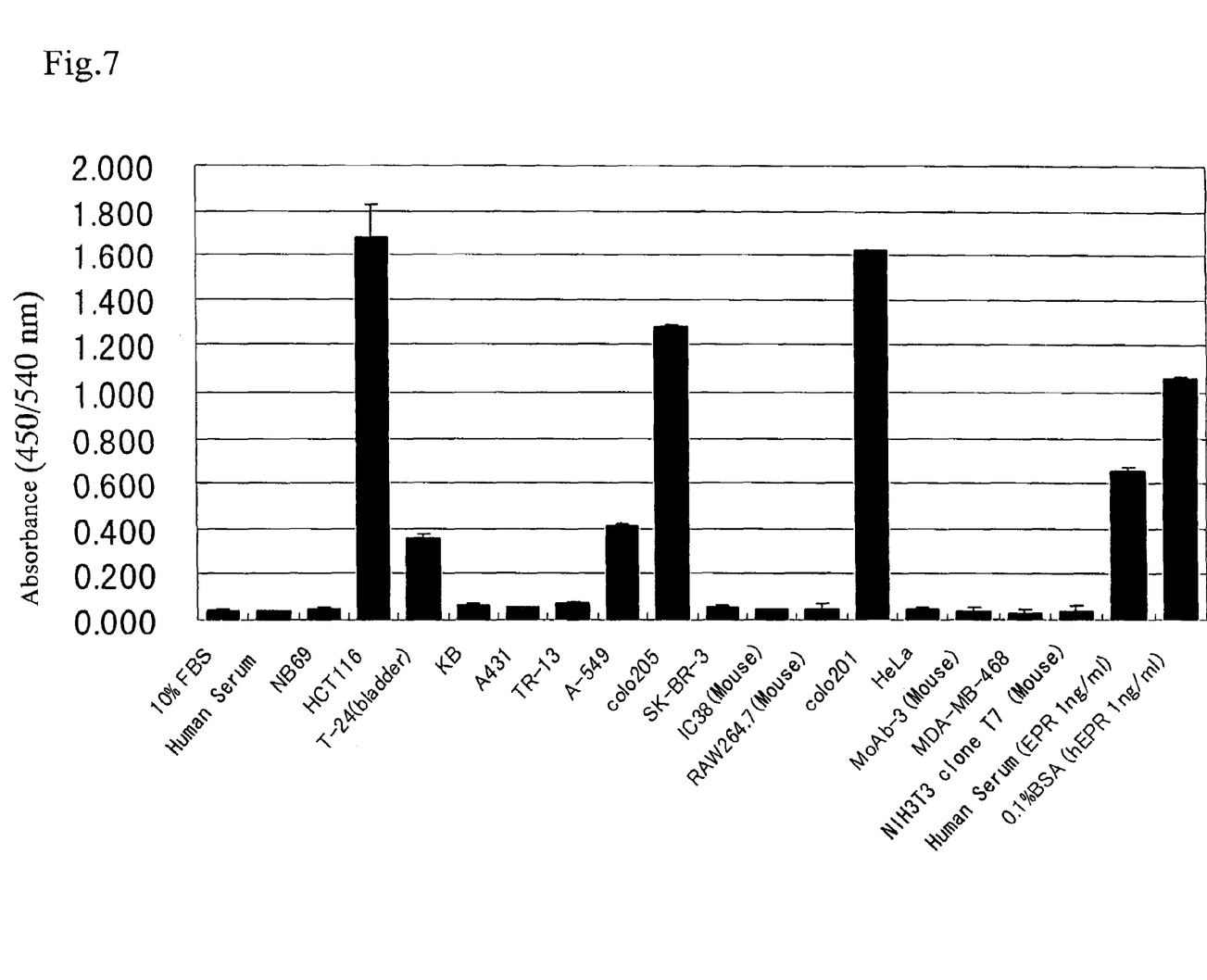
FIG. 7 shows the detection of hEPR in various cell culture media.

Results indicate that A450 nm was not observed in the culture media from mouse cells such as NIH3T3 clone T7 producing mouse EPR and others, while high production of hEPR was confirmed in human cancer cells such as A-549 (human lung cancer cells), HCT116 (human colon cancer), colo201 (human colon cancer), colo205 (human colon cancer) and T-24 (human bladder cancer) (FIG. 7), confirming that hEPR in culture media can be specifically detected. However, hEPR was not detectable in human cancer cells such as HeLa (human cervical carcinoma), NB69 (human neuroblastoma), KB (human epidermal carcinoma (oral cavity)), A431 (human epidermal carcinoma (epidermis)), SK-BR-3 (human mammary cancer), MDA-MB-468 (human mammary cancer) and TR-13 (human kidney cancer).

INDUSTRIAL APPLICABILITY

According to the present invention, it becomes possible to provide a system which detects hEPR in human blood, tissues and the like with high specificity and sensitivity and is useful for cancer diagnosis and the like to detect tumor cells expressing hEPR. Further, it is expected that the use of the method of the present invention will contribute to elucidation of the presence or absence of the hEPR expression and the relationship between the expression of hEPR and the mechanism of tumorgenesis.

All the publications, patents and patent applications herein referred to are hereby incorporated by references.

The invention claimed is:

1. A hybridoma producing a monoclonal antibody which specifically recognizes human epiregulin (hEPR), wherein the hybridoma is selected from a hybridoma having an accession number of FERM BP-08647 and a hybridoma having an accession number of FERM BP-08648.

2. A monoclonal antibody produced by the hybridoma according to claim 1.

3. A kit for detecting a human tumor comprising the monoclonal antibody according to claim 2.

* * * * *

SEQUENCE LISTING

<160> NUMBER OF SEQ ID NOS: 2

<210> SEQ ID NO 1
<211> LENGTH: 46
<212> TYPE: PRT
<213> ORGANISM: Homo sapiens

<400> SEQUENCE: 1

Val Ser Ile Thr Lys Cys Ser Ser Asp Met Asn Gly Tyr Cys Leu His
1               5                   10                  15

Gly Gln Cys Ile Tyr Leu Val Asp Met Ser Gln Asn Tyr Cys Arg Cys
            20                  25                  30

Glu Val Gly Tyr Thr Gly Val Arg Cys Glu His Phe Phe Leu
        35                  40                  45

<210> SEQ ID NO 2
<211> LENGTH: 138
<212> TYPE: DNA
<213> ORGANISM: Homo sapiens

<400> SEQUENCE: 2
gtgtcaataa caaagtgtag ctctgacatg aatggctatt gtttgcatgg acagtgcatc         60
tatctggtgg acatgagtca aaactactgc aggtgtgaag tgggttatac tggtgtccga        120
tgtgaacact tcttttta                                                     138